United States Patent
Amara et al.

(10) Patent No.: US 10,703,917 B2
(45) Date of Patent: Jul. 7, 2020

(54) COATING COMPOSITIONS SUITABLE FOR USE WITH AN OVERCOATED PHOTORESIST

(71) Applicant: Rohm and Haas Electronic Materials LLC, Marlborough, MA (US)

(72) Inventors: John P. Amara, Charlestown, MA (US); James F. Cameron, Marlborough, MA (US); Jin Wuk Sung, Worcester, MA (US); Gregory P. Prokopowicz, Worcester, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 0 days.

(21) Appl. No.: 15/652,192

(22) Filed: Jul. 17, 2017

(65) Prior Publication Data

US 2017/0313889 A1 Nov. 2, 2017

Related U.S. Application Data

(62) Division of application No. 14/537,676, filed on Nov. 10, 2014, now Pat. No. 9,708,493, which is a division of application No. 12/813,228, filed on Jun. 10, 2010, now Pat. No. 8,883,407.

(60) Provisional application No. 61/186,802, filed on Jun. 12, 2009.

(51) Int. Cl.
| | |
|---|---|
| C09D 5/00 | (2006.01) |
| H01L 21/027 | (2006.01) |
| G03F 7/16 | (2006.01) |
| G03F 7/20 | (2006.01) |
| C08F 220/36 | (2006.01) |
| G03F 7/09 | (2006.01) |
| C07C 69/76 | (2006.01) |
| C07C 69/94 | (2006.01) |
| C09D 133/14 | (2006.01) |
| G03F 7/32 | (2006.01) |

(52) U.S. Cl.
CPC ............. *C09D 5/006* (2013.01); *C07C 69/76* (2013.01); *C07C 69/94* (2013.01); *C08F 220/36* (2013.01); *C09D 133/14* (2013.01); *G03F 7/091* (2013.01); *G03F 7/16* (2013.01); *G03F 7/168* (2013.01); *G03F 7/20* (2013.01); *G03F 7/322* (2013.01); *H01L 21/0276* (2013.01)

(58) Field of Classification Search
CPC ............. G03F 7/091; G03F 7/11; C07C 69/94
See application file for complete search history.

(56) References Cited

U.S. PATENT DOCUMENTS

| | | | | |
|---|---|---|---|---|
| 3,206,398 A | * | 9/1965 | Marlowe ................ | C09K 8/605 504/157 |
| 4,130,719 A | * | 12/1978 | Cerefice ................. | C07C 51/09 528/305 |
| 5,258,532 A | * | 11/1993 | Lawson .................. | C07C 65/11 556/132 |
| 5,925,487 A | * | 7/1999 | Fawkes .................. | C07C 65/11 430/108.2 |
| 6,808,869 B1 | | 10/2004 | Mizutani et al. | |
| 8,883,407 B2 | * | 11/2014 | Amara .................. | C08F 220/36 430/271.1 |
| 8,940,472 B2 | * | 1/2015 | Cameron ............... | G03F 7/091 430/271.1 |
| 9,708,493 B2 | * | 7/2017 | Amara .................. | C09D 5/006 |
| 2004/0072420 A1 | * | 4/2004 | Enomoto ............... | G03F 7/091 438/636 |
| 2005/0026068 A1 | * | 2/2005 | Gogolides .............. | C07C 69/40 430/270.1 |
| 2007/0004228 A1 | | 1/2007 | Hatanaka et al. | |
| 2008/0138744 A1 | * | 6/2008 | Hatanaka .............. | G03F 7/0392 430/319 |
| 2008/0160460 A1 | | 7/2008 | Yoon et al. | |
| 2009/0111057 A1 | | 4/2009 | Xu et al. | |
| 2009/0148717 A1 | | 6/2009 | Jen et al. | |
| 2017/0108776 A1 | * | 4/2017 | Cameron ............... | G03F 7/091 |

FOREIGN PATENT DOCUMENTS

| | | | |
|---|---|---|---|
| CA | 737492 A | * | 6/1966 |
| EP | 2216683 A2 | | 8/2010 |
| JP | 2001-109150 A | | 4/2001 |
| JP | 2004-212907 A | | 7/2004 |

(Continued)

OTHER PUBLICATIONS

Simionescu et al, Copolymerization of 9-anthrylmethyl methacrylate with N-phenylmaleimide, Makromol. Chem, vol. 186, No. 6, pp. 1121-1128, (Jun. 1985).*
English translation of JP, 2004-212907, A (2004) from machine translation from AIPN Japan Patent Office National Center for Industrial Property Information and Training, generated Feb. 4, 2013, 25 pages.*
Durmaz, et al. (2006), Preparation of block copolymers via Diels Alder reaction of maleimide- and anthracene-end functionalized polymers. J. Polym. Sci. A Polym. Chem., 44:1667-1675. doi: 10.1002/pola.21275 published on line Jan. 26, 2006. http://o n li n elib rary.wiley.com/doi/10.1002/pola.21275/abstract.*

(Continued)

*Primary Examiner* — Cynthia Hamilton
(74) *Attorney, Agent, or Firm* — Mintz Levin Cohn Ferris Glovsky and Popeo, P.C.; Peter F. Corless

(57) ABSTRACT

In one aspect, organic coating compositions, particularly antireflective coating compositions, are provided that comprise that comprise a diene/dienophile reaction product. In another aspect, organic coating compositions, particularly antireflective coating compositions, are provided that comprise a component comprising a hydroxyl-naphthoic group, such as a 6-hydroxy-2-naphthoic group Preferred compositions of the invention are useful to reduce reflection of exposing radiation from a substrate back into an overcoated photoresist layer and/or function as a planarizing, conformal or via-fill layer.

7 Claims, No Drawings

(56) References Cited

FOREIGN PATENT DOCUMENTS

WO          2004041760 A2     5/2004

OTHER PUBLICATIONS

English translation of JP, 2001-109150, A (2001) from machine translation from AIPN Japan Patent Office National Center for Industrial Property Information and Training, generated Feb. 4, 2013, 83 pages.*
Shindo et al, "Hydroxylations of substituted naphthalenes by *Escherichia coli* expressing aromatic dihydroxylating dioxygenase genes from polycyclic aromatic hydrocarbon-utilizing marine bacteria", Journal of Molecular Catalysis B: Enzymatic 48 (2007) 77-83.*
English Translation of Examination Report dated Feb. 7, 2013 in connection with corresponding Taiwanese Patent Application No. 99119036.
English Translation of the First Office Action dated Apr. 3, 2013 in connection with corresponding Chinese Patent Application No. 201010263243.6.
Search Report, Examination Report and Response for corresponding European Patent Application No. 10165624.7.

* cited by examiner

COATING COMPOSITIONS SUITABLE FOR USE WITH AN OVERCOATED PHOTORESIST

This application is a divisional application of U.S. application Ser. No. 14/537,676, filed Nov. 10, 2014 which is a divisional application of U.S. application Ser. No. 12/813,228, filed Jun. 10, 2010 which claims the benefit of priority under 35 U.S.C. § 119(e) to U.S. Provisional Application No. 61/186,802, filed Jun. 12, 2009, the contents of which are incorporated herein by reference.

The present invention relates to compositions (including antireflective coating compositions or "ARCs") that can reduce reflection of exposing radiation from a substrate back into an overcoated photoresist layer and/or function as a planarizing, conformal or via-fill layer. More particularly, in one aspect, the invention relates to organic coating compositions, particularly antireflective coating compositions, that comprise a diene/dienophile reaction product. In another aspect, the invention relates to relates to organic coating compositions, particularly antireflective coating compositions, that comprise a component comprising a hydroxylnaphthoic group, such as a 6-hydroxy-2-naphthoic group.

Photoresists are photosensitive films used for the transfer of images to a substrate. A coating layer of a photoresist is formed on a substrate and the photoresist layer is then exposed through a photomask to a source of activating radiation. Following exposure, the photoresist is developed to provide a relief image that permits selective processing of a substrate.

A major use of photoresists is in semiconductor manufacture where an object is to convert a highly polished semiconductor slice, such as silicon or gallium arsenide, into a complex matrix of electron conducting paths, preferably of micron or submicron geometry, that perform circuit functions. Proper photoresist processing is a key to attaining this object. While there is a strong interdependency among the various photoresist processing steps, exposure is believed to be one of the most important steps in attaining high resolution photoresist images.

Reflection of activating radiation used to expose a photoresist often poses limits on resolution of the image patterned in the photoresist layer. Reflection of radiation from the substrate/photoresist interface can produce spatial variations in the radiation intensity in the photoresist, resulting in non-uniform photoresist linewidth upon development. Radiation also can scatter from the substrate/photoresist interface into regions of the photoresist where exposure is not intended, again resulting in linewidth variations. The amount of scattering and reflection will typically vary from region to region, resulting in further linewidth non-uniformity. Variations in substrate topography also can give rise to resolution-limiting problems.

One approach used to reduce the problem of reflected radiation has been the use of a radiation absorbing layer interposed between the substrate surface and the photoresist coating layer.

While current organic antireflective coating compositions are highly effective for many applications, it is also frequently desired to have particular antireflective compositions to meet specific processing requirements. For instance, it may be desired to remove an antireflective layer that has been bared of overcoated photoresist (e.g. with a positive resist, exposed resist areas removed by alkaline aqueous developer) by means other than a plasma etchant. See U.S. Pat. No. 6,844,131 and U.S. Patent Publication US20050181299. Such approaches offer the potential of avoiding additional processing steps and pitfalls associated with plasma etchant removal of a bottom antireflective coating layer.

It would be desirable to have new compositions that could be used as underlying antireflective coating layer in the manufacture of microelectronic wafers. It would be particularly desirable to have new compositions that could be used as underlying antireflective coating layer and could be removed with an aqueous photoresist developer.

We have now discovered new coating compositions that are particularly useful as underlying antireflective coating layers for an overcoated photoresist layer.

More particularly, in a first aspect, the invention provides compositions that comprise a component (sometimes referred to herein as a "reaction product component") that is a reaction product of a diene and a dienophile. Preferred dienes and dienophile both have unsaturated groups and preferably can combine to form a cyclic adduct in which there is a net reduction of the bond multiplicity. Preferred dienes are electron-rich include carbocyclic or heteroaromatic groups, including multiple ring carbocyclic or heteroaromatic groups, particularly fused ring groups such as anthracene or pentacene groups. Preferred dienophiles include groups that comprise olefin moieties that have proximate (e.g. within 1, 2, or 3 atoms) electron-withdrawing substituent(s) e.g. preferred dienophiles include groups that comprise one or more α,β-unsaturated groups. Specifically preferred dienophiles include imide-containing groups particularly maleimdes, anhydrides such as maleic anhydride, and other groups such as dimethylacetylene dicarboxylate.

In preferred aspect, the invention provides compositions that comprise a reaction product component that is a Diels Alder reaction product of a diene and a dienophile as discussed above. The term "Diels Alder reaction" is used herein in accordance with its well-recognized meaning, i.e. a (4+2) cycloaddition, e.g. as refereed to under the definition of "cycloaddition" in *Compendium of Chemical Technology*, IUPAC Recommendations, 2" edition (1997 Blackwell Science). Preferred Diels Alder reaction products include a reaction product of (i) an imide-containing compound e.g. maleimide or other dienophiles e.g. anhydrides such as maleic anhydride, and other groups such as dimethylacetylene dicarboxylate and (ii) a polycyclic aromatic group. Particularly preferred Diels Alder reaction products include a reaction product of (1) an imide-containing compound e.g. maleimide or other dienophiles e.g. anhydrides such as maleic anhydride, and other groups such as dimethylacetylene dicarboxylate and (2) an anthracene or pentacene group.

Generally preferred reaction product components of an underlying coating composition of the invention are resins, including homopolymers as well as mixed polymers such as copolymers (two distinct repeat units), terpolymers (three distinct repeat units), tetrapolymers (four distinct repeat units), pentapolymers (five distinct repeat units) and other higher order polymers.

In certain aspects, particularly preferred reaction products components are resins that comprise at least three or four distinct functional groups that can impart the following properties (1) dissolution rate inhibition; (2) strip resistance (e.g.); (3) desired aqueous alkaline developer solubility (e.g. a photoacid-labile group such as a photoacid-labile ester (e.g. —C(=O)OC(CH$_3$)$_3$) or an acetal moiety); and (4) a chromophore group to absorb undesired reflections of photoresist exposure radiation (e.g. a carbocyclic aryl group such as optionally substituted phenyl, naphthyl or anthraceny 1).

Significantly, preferred processed coating compositions of the invention may be removed to expose an underlying surface with an aqueous alkaline developer used for development of an overcoated photoresist layer. This offers a number of notable advantages, including reducing the additional processing step and costs required with use of a plasma etchant to remove the underlying coating layer.

In another aspect, organic coating compositions are provided, particularly antireflective coating compositions, that comprise a component comprising a hydroxyl-naphthoic group (e.g. $C_9H_6(OH)(COO-)$, such as a 6-hydroxy-2-naphthoic group. In preferred aspects, as referred to herein, a hydroxyl-naphthoic moiety or other similar term refers to a naphthyl moiety that has both hydroxyl (—OH) and carboxy (—C(=OO—) ring substituents, and may have additional non-hydrogen ring substituents such as e.g. halo (e.g. F, Cl, Br, I), alkoxy such as optionally substituted $C_{1-12}$alkoxy, alkyl such as optionally substituted $C_{1-12}$alkoxy, and the like.

In a preferred embodiment, multiple aspects of the invention are used in combination. More particularly, a preferred embodiments includes organic coating compositions are provided, particularly antireflective coating compositions, that comprise a component that comprises (1) a hydroxyl-naphthoic group, such as a 6-hydroxy-2-naphthoic group and (2) a reaction product of a diene and a dienophile as disclosed herein. In a particular preferred system, the underlying coating composition may comprise a resin that comprises multiple repeat units that comprise (1) a hydroxyl-naphthoic group, such as a 6-hydroxy-2-naphthoic group and (2) a reaction product of a diene and a dienophile as disclosed herein.

It has been found that hydroxyl-naphthoic groups, such as a 6-hydroxy-2-naphthoic group, can be effective chromophores of undesired reflections of exposure of an overcoated photoresist layer.

Coating compositions of the invention also may optionally contain one or more other materials in addition to the reaction component and/or a component that comprises a hydroxyl-naphthoic group. For example, a coating composition of the invention may contain an additional component that comprises chromophore groups that can absorb undesired radiation used to expose the overcoated resist layer from reflecting back into the resist layer. Such chromophore groups may be present a variety of composition components including the reaction component itself or an additional component may comprise chromophore groups such as an added resin which may have chromophore groups as backbone members or as pendant groups, and/or an added small molecule (e.g. MW less than about 1000 or 500) that contains one or more chromophore moieties.

Generally preferred chromophores for inclusion in coating composition of the invention particularly those used for antireflective applications include both single ring and multiple ring aromatic groups such as optionally substituted phenyl, optionally substituted naphthyl, optionally substituted anthracenyl, optionally substituted phenanthracenyl, optionally substituted quinolinyl, and the like. Particularly preferred chromophores may vary with the radiation employed to expose an overcoated resist layer. More specifically, for exposure of an overcoated resist at 248 nm, optionally substituted anthracene and optionally substituted naphthyl are preferred chromophores of the antireflective composition. For exposure of an overcoated resist at 193 nm, optionally substituted phenyl and optionally substituted naphthyl are particularly preferred chromophores.

Coating compositions of the invention also may optionally comprise an acid or acid generator compound (e.g. photoacid generator and/or thermal acid generator) to facilitate reaction of composition component(s) during lithographic thermal processing of an applied composition coating layer. A photoacid generator compound (i.e. a compound that can generate acid upon exposure to activating radiation such as 193 nm) and/or othermal acid generator compound (i.e. a compound that can generate acid upon thermal treatment) is generally suitable.

Photoacid generator compound(s) included in an underlying coating composition can generate acid upon treatment with radiation used to expose an overcoated photoresist layer. By such use of photoacid generator compound(s), acid is not liberated from the photoacid generator compound(s) prior to application of a photoresist layer over the underlying coating composition. Exposure of the applied resist layer to patterned activating radiation liberates acid from the coating composition photoacid generator compound(s) and can enhance resolution of the resist image patterned over the coating composition layer by compensating for photoacid at the resist/coating composition that may diffuse from the resist into the coating composition as well as facilitate desired selective development of the underlying coating composition during treatment with an aqueous alkaline developer.

A coating composition may be provided by an admixture of a reaction component and/or a component that comprises a hydroxyl-naphthoic group (which may include a single material e.g. a resin that comprises together with one or more optional components as discussed above in a solvent component. The solvent component suitably may be one or more organic solvents such as one or more alcohol solvents e.g. ethyl lactate, propylene glycol methyl ether (1-methoxy-2-propanol), methyl-2-hydroxyisobutyrate, and the like, and/or one more non-hydroxy solvents such as ethyl ethoxy propionate, propylene glycol methyl ether acetate (1-methoxy-2-propanol acetate), and the like.

The coating composition is then applied such as by spin-coating (i.e. a spin-on composition) to a substrate such as a microelectronic semiconductor wafer. The solvent carrier may be removed by heating, e.g. 170° C. to 250° C. on a vacuum hotplate.

A variety of photoresists may be used in combination (i.e. overcoated) with a coating composition of the invention. Preferred photoresists for use with the antireflective compositions of the invention are chemically-amplified resists, especially positive-acting photoresists that contain one or more photoacid generator compounds and a resin component that contains units that undergo a deblocking or cleavage reaction in the presence of photogenerated acid, such as photoacid-labile ester, acetal, ketal or ether units. Preferred photoresists for use with a coating composition of the invention may be imaged with relatively short-wavelength radiation, e.g. radiation having a wavelength of less than 300 nm or less than 260 nm such as about 248 nm, or radiation having a wavelength of less than about 200 nm, such as 193 nm or 157 nm. Other useful exposure energies include EUV, e-beam, IPL, and x-ray exposures. The invention further provides methods for forming a photoresist relief image and novel articles of manufacture comprising substrates (such as a microelectronic wafer substrate) coated with an antireflective composition of the invention alone or in combination with a photoresist composition. As discussed above, a processed underlying coating composition layer may be removed with the same aqueous, alkaline developer solution used to develop an overcoated photoresist layer, i.e. both the exposed photoresist layer and underlying cured coating composition can be removed in a single step with an aqueous alkaline developer in those regions defined by the photomask during exposure.

More particularly, preferred methods of the invention may include:

1. Applying a coating layer of a composition that comprises one or more reaction components and/or components that comprises a hydroxyl-naphthoic group as discussed above. The composition coating layer may be applied over a variety of substrates including a microelectronic wafer;

2. Preferably thermally treating the applied composition coating layer. The thermal treatment can remove casting solvent of the coating composition and render that composition layer substantially insoluble in photoresist casting solvents such as ethyl lactate, propylene glycol methyl ether acetate, 2-heptanone, and the like;

3. Applying a photoresist composition coating layer over the thermally baked underlying composition coating layer. The applied photoresist layer is exposed to activating radiation such as radiation having a wavelength of below 300 nm such as 248 nm, or below 200 run such as 193 nm, typically through a photomask to form a patterned image in the resist layer. The exposed photoresist may be thermally treated as needed to enhance or form the latent image;

4. The exposed photoresist layer is then treated with a developer solution, such as an aqueous, alkaline developer solution. The developer solution can remove the image defined in the resist layer as well as matching region of the underlying coating composition layer, i.e. where a relief image is defined through both the photoresist layer and the underlying coating composition layer.

In preferred aspects an underlying coating composition of the invention is used in combination with a positive-acting photoresist, e.g. as may be imaged at sub-300 nm and sub-200 nm wavelengths such as 248 nm or 193 nm. Chemically-amplified positive resists are preferred, which contain a component that has moieties that will undergo a deblocking or cleavage reaction in the presence of photo-generated acid, such as photoacid-labile esters or acetals. Preferred positive-acting photoresists for sub-300 nm imaging such as 248 nm comprise a polymer that comprises phenolic units and acid-labile esters and/or acetal moieties and a photoacid generator compound. Preferred positive-acting photoresists for use at sub-200 nm imaging such as 193 nm imaging are substantially free of aromatic groups, particularly resins that contain phenyl or other aromatic substitution.

In another aspect, the invention also includes methods for producing a coating composition of the invention, and methods for forming a photoresist relief image and methods for manufacturing an electronic device such as a processed microelectronic wafer.

In yet another aspect of the invention, compounds (such as a resin) are provided which comprise one or more groups of the following formulae:

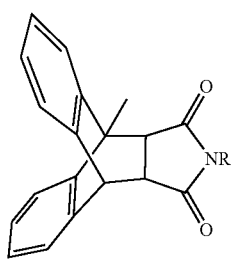

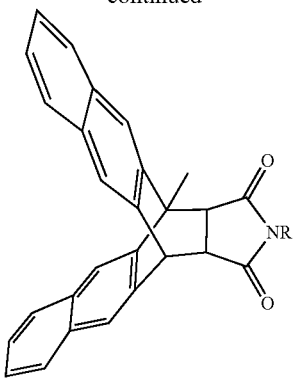

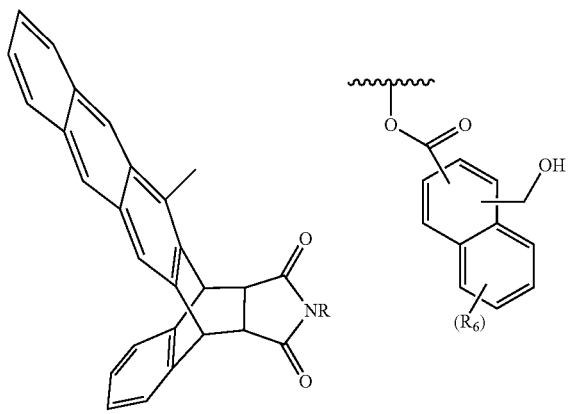

where in the above formulae each R is independently hydrogen or a non-hydrogen such as e.g. =H, $C_{1-18}$alkyl including methyl, aryl (including carbocyclic aryl such as phenyl, naphthyl), and $C_{1-18}$alkoxy.

Preferred compounds of the above formulae include resins, where one or more repeat units may comprise one or more of the above groups. For instance, the following preferred acrylate compounds may be polymerized with other reactive monomers to provide a resin comprising polymerized units:

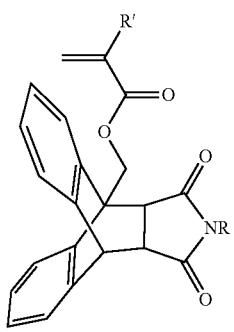

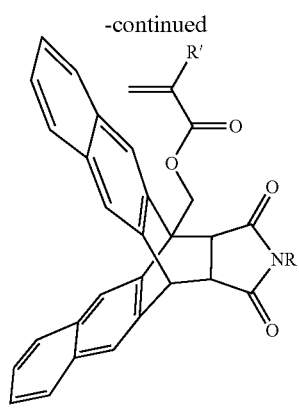

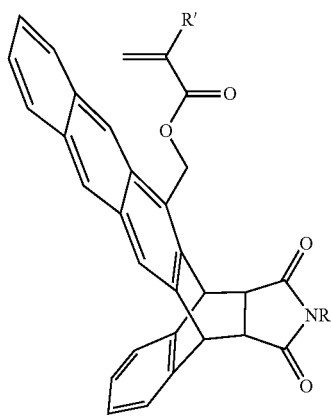

where in the above formulae each R is independently hydrogen or a non-hydrogen such as e.g. =H, $C_{1-18}$alkyl including methyl, aryl (including carbocyclic aryl such as phenyl, naphthyl), and $C_{1-18}$alkoxy; and R' is hydrogen or $C_{1-6}$alkyl such as methyl.

Other aspects of the invention are disclosed infra.

As discussed above, we now provide new organic coating compositions that are particularly useful with an overcoated photoresist layer. Preferred coating compositions of the invention may be applied by spin-coating (spin-on compositions) and formulated as a solvent composition. The coating compositions of the invention are especially useful as antireflective compositions for an overcoated photoresist.

Underlying Coating Compositions

As discussed above, in a first aspect, underlying coating compositions comprise reaction product component that is a reaction product of a diene and a dienophile. In another aspect, underlying coating compositions comprise a reaction product component that is a Diels Alder reaction product. Suitably, reaction product components are resins, including both homopolymers as well as higher order polymers such as copolymers, terpolymers, tetrapolymers and pentapolymers.

In another aspect, organic coating compositions are provided, particularly antireflective coating compositions, that comprise a component comprising a hydroxyl-naphthoic group, such as a 6-hydroxy-2-naphthoic group.

Preferred hydroxyl-naphthoic groups include the following structures:

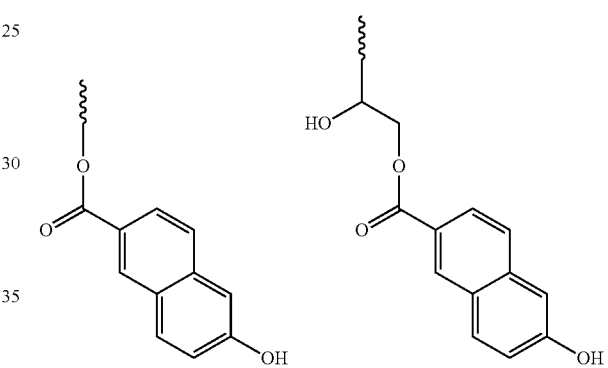

Preferred resins that comprise hydroxyl-naphthoic groups for use in an underlying coating composition include resins that comprise the following structure (pentapolymer):

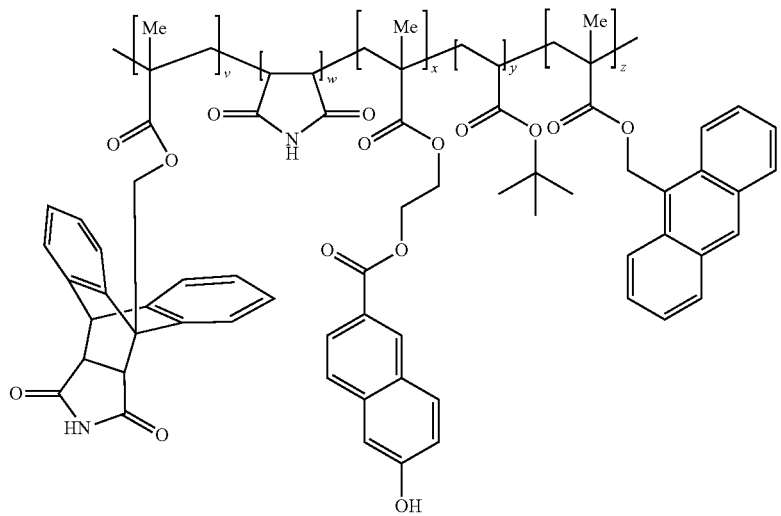

Preferred syntheses of monomers and components such as resins that comprise a hydroxyl-naphthoic group, such as a 6-hydroxy-2-naphthoic group are set forth in the examples which follow.

Reaction product components can be synthesized by a variety of methods. For instance, a monomer can be preferred that is a Diels Alder reaction product of two materials. That monomer then can be reacted with other monomers to provide a resin component of an underlying coating composition of the invention. Diels Alder and other cycloaddition reactions are known.

Alternatively, a formed resin containing either or both a diene (e.g. anthracene or pentacene) and a dienophile (e.g. a substrate comprising an olefin with one or more electron-withdrawing substituents, such as maleimide, maleic anhydride or dimethylacetylene dicarboxylate) can undergo a cycloaddition reaction to provide a reaction product component of an underlying coating composition of the invention. See, for instance, Examples 4-6 which follow for exemplary syntheses of a reaction product component from a pre-formed polymer.

More particularly, the following Scheme 1 depicts an exemplary monomer modified via Diels Alder reaction that can be polymerized to provide a resin reaction product component of an underlying coating composition of the invention.

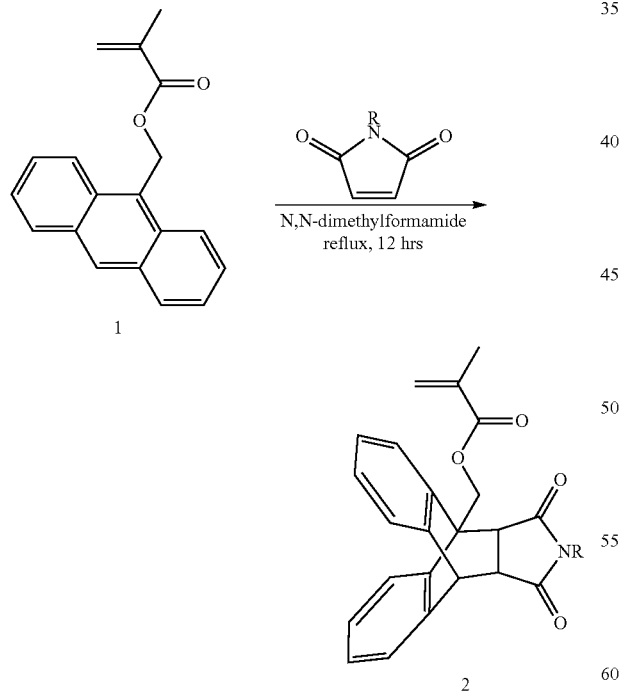

Scheme 1. The Diels-Alder reaction of anthracenemethylmethyacrylate monomer, 1, with N-substitued maleimides (R = H, optionally substituted $C_{1-18}$alkyl including, optionally substituted methyl, optionally substituted aryl (including optionally substituted carbocyclic aryl such as phenyl, naphthyl), optionally substituted $C_{1-18}$alkoxy, and the like)

Scheme 1 above depicts the cycloaddition (particularly, Diels-Alder) reaction of anthracenemethylmethacrylate monomer, 1, with a N-substituted maleimide to afford a modified methacrylic monomer, 2, with a pendant maleimide functionality. Monomer 2 can provide strong absorbance at 193 nm due to the two benzo-fused aromatic substituents. Additionally, the pendant maleimide adduct can impact base dissolution characteristics and solvent strip resistance to an otherwise solvent soluble and base insoluble monomer 1.

Under the reaction conditions shown in Scheme 1 (refluxing dioxane, 12 hrs), it has been found that the depicted cycloaddition reaction proceeds readily. See also the examples which follow for exemplary preferred reaction conditions.

The following Scheme 2 depicts an exemplary monomer modified via Diels Alder reaction that can be polymerized to provide a resin reaction product component of an underlying coating composition of the invention.

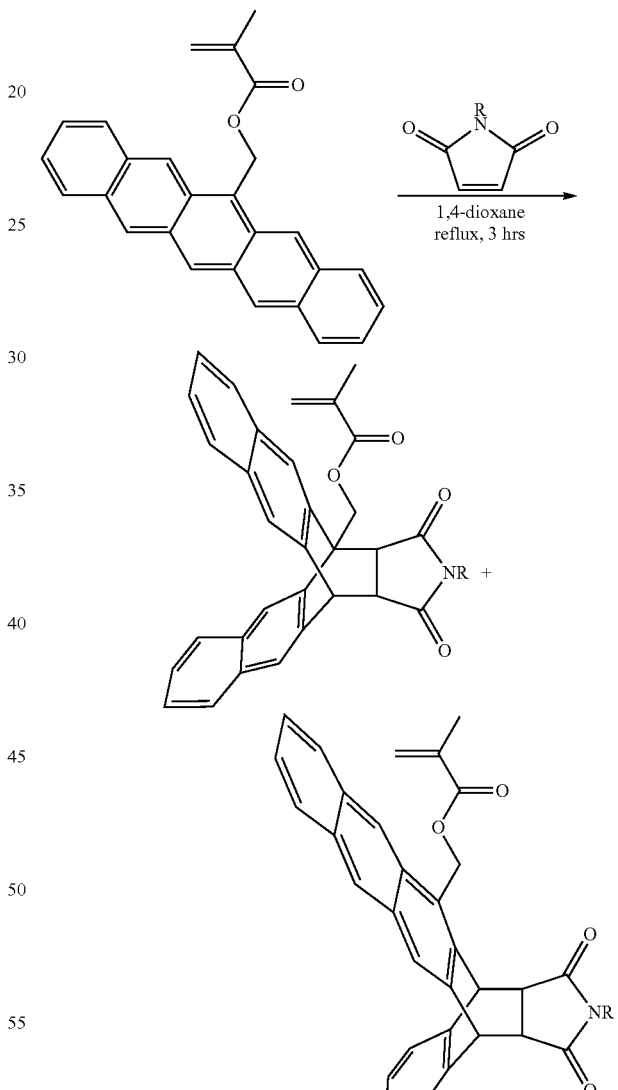

The Diels-Alder reaction of pentacenemethylmethyacrylate monomer, with N-substituted maleimides (R = H, optionally substituted $C_{1-18}$alkyl including, optionally substituted methyl, optionally substituted aryl (including optionally substituted carbocyclic aryl such as phenyl, naphthyl), optionally substituted $C_{1-18}$alkoxy, and the like)

Scheme 2 above depicts the cycloaddition (particularly, Diels-Alder) reaction of pentacenenthracenemethylmethacrylate monomer with a N-substituted maleimide to afford a modified methacrylic monomer with a pendant maleimide functionality. Monomer 2 can provide strong absorbance at 193 nm due to the two benzo-fused aromatic substituents. Additionally, the pendant maleimide adduct can impact base dissolution characteristics and solvent strip resistance to an otherwise solvent soluble and base insoluble pentacenenthracenemethylmethacrylate monomer.

As discussed above, preferably regions of a layer of an underlying coating composition can be selectively removed with an aqueous alkaline developer composition (e.g. 0.26N tetramethyl ammonium hydroxide aqueous developer solution). Preferred reaction product components are polymers with multiple, distinct functional groups.

Preferred underlying coating compositions of the invention do not undergo significant crosslinking (molecular weight increases of composition component(s)) upon thermal treatment such as 180° C. or 240° C. for 1 to 5 minutes. See Example 15 which follows for a protocol for assessing whether a coating layer does not undergo substantial crosslinking.

Preferred reaction product components of an underlying coating composition comprise one or more photoacid-labile group which can undergo a cleavage or deprotection reaction to provide functional group(s) which promote aqueous alkaline-developer solubility, such as carboxy, fluorinated alcohol, phenols, imides, sulfonamides, and other such moieties. Upon image-wise exposure and post-exposure bake of an overcoated photoresist layer, the photoacid-labile groups of the reaction component(s) and/or component(s) that comprises a hydroxyl-naphthoic group of the underlying coating composition can react and liberate functional group(s) which promote aqueous alkaline-developer solubility.

Preferably, a reaction product component of an underlying coating composition contains other functional groups in addition to acid labile groups, such as chromophore component in carrier solvent(s) of an overcoated photoresist layer); dissolution ratepromoters (do not contain photoacid-labile groups but nevertheless can promote dissolution rate in aqueous alkaline developer; acid-labile groups); and the like.

More particularly, preferred functional groups of a reaction product component include the following:

1. Chromophore groups: An organic functional group with sufficient absorbance at 248 nm (KrF exposure) or 193 nm (ArF exposure) to provide for reflection control in antireflective applications. Various substituted anthracenes, naphthalenes, and phenyl groups are examples of preferred chromophores. Such chromophores may be incorporated into a polymer using the following monomers: anthracene methyl methacrylate (ANTMA), hydroxystyrene monomer (PHS), acetoxy-styrene monomer (4AS), hydroxyvinyl-naphthalene monomer (HVN), and 2-Methyl-acrylic acid 6-hydroxy-naphthalen-2-ylmethyl ester.

2. Solvent strip resistance groups. An organic functional group that, as a component of a polymer, decreases the rate of dissolution of the polymer in the various selected organic solvents that are commonly employed in KrF and ArF-type resist formulations. These include PGMEA, ethyl lactate, and hydroxy isobutyric acid methyl ester. Solvent strip resistance groups can permit the application of an over-coated photoresist layer to the underlayer without intermixing. Various substituted amides, lactones, carboxylic acids, carboxylic acid esters and other hydrolysable groups are examples of functional groups that can provide solvent strip resistance to a polymer-based underlayer composition. Such solvent strip resistance promoters may be incorporated into a polymer using the following exemplary monomers: maleimide, norbornyl lactone acrylate monomer (NLA), norbornyl lactone methacrylate monomer (NLM), and anthracenemethylmethacrylate-maleimide cycloadduct (ANT-MI).

3. Dissolution rate promoter groups. An organic functional group that, as a component of a polymer, promotes (increases) the rate of dissolution of the polymer in aqueous tetramethylammonium hydroxide solution (0.26N). Various substituted imides, amides, phenols, sulfonamides, fluorinated alcohols including hexfluoroalcohols (e.g. $-C(CF_3)_2OH$), groups are examples of preferred dissolution rate promoters. Such dissolution rate promoters may be incorporated into a polymer using the following monomers: maleimide, hydroxystyrene monomer, acetoxystyrene monomer, hydroxyvinylnaphthalene monomer, norbornyl lactone acrylate monomer (NLA), norbornyl lactone methacrylate monomer (NLM), and anthracenemethylmethacrylate-maleimide cycloadduct (ANT-MI).

4. Acid-labile groups. An organic functional group that, as a component of apolymer, may undergo an acid-catalyzed deprotection reaction. In these applications, the acid-catalyst is provided by means of a photo-acid generator (PAG), which provides acid in the exposed regions during the photolithographic processing of an over-coatedphotoresist. The deprotection reaction significantly increases the rate of dissolution of the polymer in developer solutions, permitting the removal of the photoresist and the underlying coating compositions in exposed areas with good pattern fidelity. The fast dissolution rate in aqueous developer solutions, provided by the de-protected acid labile groups, eliminates or at least minimizes any underlying coating composition residue or scumming observed in the exposed regions after development. The acid-catalyzed de-protection reaction of tert-butyl acrylate esters is a preferred example.

Suitable molecular weights of resin reaction product components of underlying coating compositions of the invention may vary rather widely, e.g. suitably weight average molecular weights may range from about 1,000 to 50,000, more preferably about 1,500 to 10,000, 20,000 or 30,000.

Exemplary reaction product components for use in the present underlying coating compositions are set forth in the examples which follow as well as Schemes 1 and 2 above.

As discussed above, particularly preferred underlying coating compositions of the invention additionally may comprise one or more photoacid generator compounds. Activation of the photoacid generator compound(s) during image-wise exposure a an overcoated photoresist layer can result in reaction of acid-labile groups of the reaction component(s) of the underlying coating composition and enable subsequent one-step development of both the imaged photoresist and underlying coating composition layers.

A wide variety of photoacid generator compounds may be employed in an underlying coating compositions including ionic and compounds e.g. onium salts (such as sulfonium and/or iodonium compounds), and non-ionic photoacid generators such as imidosulfonates, N-sulfonyloxyimides, disulfone compounds, and nitrobenzyl-based photoacid generators, and other photoacid generators that have been used in photoresist compositions. Specifically suitable photoacid generator compounds for use in the present coating compositions include those identified below for use in photoresist compositions as well as the ionic and non-ionic photoacid generators disclosed in U.S. Pat. Nos. 6,20,911 and 6,803,169, such as sulfonium compounds including triphenyl sulfonium salts, iodonium compounds including diphenyl iodonium compounds and imidosulfonates and other non-ionic photoacid generator compounds.

One or more photoacid generators may be employed in an underlying coating composition in a variety of amounts, e.g. where the one or more photoacid generator compounds are percent in amounts of about 5 weight percent or less based on total solids (all components except solvent carrier) of an underlying coating composition, suitably less than 4, 3, 2 or even 1 weight percent of total solids of an underlying coating composition. Another optional additive of underlying coating compositions of invention, particularly when one or more photoacid generator compounds are present in such composition is an added base, e.g. tetrabutylammonium hydroxide (TBAH), or tetrabutylammonium lactate, or a hindered amine such as diazabicyclo undecene or diazabicyclononene. The added base is suitably used in relatively small amounts, e.g. about 0.03 to 5 percent by weight relative to the total solids of the underlying coating composition.

Coating compositions of the invention, particularly for reflection control applications, also may contain additional dye compounds that absorb radiation used to expose an overcoated photoresist layer. Other optional additives include surface leveling agents, for example, the leveling agent available under the tradename Silwet 7604 from Union Carbide, or the surfactant FC 171 or FC 431 available from the 3M Company, or PF656 surfactant from Omnova.

Still further optional additives of an underlying coating composition are one or more resins in addition to and distinct from any resins of the resin product component. For instance, a polyester or acrylate-based resin that comprises desired chromophore groups (e.g. anthracene, phenyl or naphthyl) may be included in a composition both to provide the chromophore function (i.e. absorption of undesired reflection of exposure radiation) as well as film-forming properties to the applied composition.

As discussed above, a coating composition of the invention is suitably formulated as a liquid spin-on composition and contain one or more blended solvents. Suitable solvents include e.g. a lactate such as ethyl lactate or methyl lactate, an acetate such as amyl acetate, anisole, one or more of the glycol ethers such as 2-methoxyethyl ether (diglyme), ethylene glycol monomethyl ether, and propylene glycol monomethyl ether; solvents that have both ether and hydroxy moieties such as methoxy butanol, ethoxy butanol, methoxy propanol, and ethoxy propanol; esters such as methyl cellosolve acetate, ethyl cellosolve acetate, methyl-2-hydroxyisobutyrate, propylene glycol monomethyl ether acetate, dipropylene glycol monomethyl ether acetate and other solvents such as dibasic esters, propylene carbonate and gamma-butyrolactone, ketones such as heptanone (particularly 2-heptanone) and cyclohexanone, and the like.

To make a liquid coating composition of the invention, the component(s) of the coating composition are dissolved in a suitable solvent such as, for example, one or more of ethyl lactate, propylene glycol methyl ester acetate, and/or methyl-2-hydroxyisobutyrate. The preferred concentration of the dry component(s) in the solvent will depend on several factors such as the method of application. In general, the solids content of a coating composition varies from about 0.5 to 20 weight percent of the total weight of the coating composition, preferably the solids content varies from about 1 to 10 weight of the coating composition. Of the total solids (all materials except solvent carrier) of an underlaying coating composition, the reaction product component (e.g. one or more resins) may comprises the majority of the weight of total solids of the composition, e.g. where 60, 70, 80, 90, 95 or more weight percent of a coating composition is comprised of the reaction product component. See the examples which follow for exemplary preferred amounts of materials of underlying coating compositions of the invention.

Photoresist Compositions

A variety of photoresist compositions can be employed with coating compositions of the invention, including positive-acting photoacid-generating compositions, as discussed above. Photoresists used with coating compositions of the invention typically comprise a resin and a photoactive component, typically a photoacid generator compound. Preferably the photoresist resin binder has functional groups that impart alkaline aqueous developability to the imaged resist composition.

As discussed above, particularly preferred photoresists for use with coating compositions of the invention include chemically-amplified resists, including positive acting chemically-amplified resist compositions, where the photoactivated acid in the resist layer induces a deprotection-type reaction of one or more composition components to thereby provide solubility differentials between exposed and unexposed regions of the resist coating layer. A number of chemically-amplified resist compositions have been described, e.g., in U.S. Pat. Nos. 4,968,581; 4,883,740; 4,810,613; 4,491,628 and 5,492,793, all of which are incorporated herein by reference for their teaching of making and using chemically amplified positive-acting resists.

Coating compositions of the invention also may be used with other positive resists, including those that contain resin binders that comprise polar functional groups such as hydroxyl or carboxyl and the resin is used in a resist composition in an amount sufficient to render the resist developable with an aqueous alkaline solution. Generally preferred resist resins are phenolic resins including phenol aldehyde condensates known in the art as novolak resins, homo and copolymers or alkenyl phenols and homo and copolymers of N-hydroxyphenyl-maleimides as well as copolymers of fluorinated alcohols including hexafluoroalcohols (e.g. —$C(CF_3)_2OH$—).

Preferred positive-acting photoresists for use with an underlying coating composition of the invention contains an imaging-effective amount of photoacid generator compounds and one or more resins that are selected from the group of:

1) a phenolic resin that contains acid-labile groups that can provide a chemically amplified positive resist particularly suitable for imaging at 248 nm. Particularly preferred resins of this class include: i) polymers that contain polymerized units of a vinyl phenol and an alkyl acrylate, where the polymerized alkyl acrylate units can undergo a deblocking reaction in the presence of photoacid. Exemplary alkyl acrylates that can undergo a photoacid-induced deblocking reaction include e.g. t-butyl acrylate, t-butyl methacrylate, methyladamantyl acrylate, methyl adamantyl methacrylate, and other non-cyclic alkyl and alicyclic acrylates that can undergo a photoacid-induced reaction, such as polymers in U.S. Pat. Nos. 6,042,997 and 5,492,793, incorporated herein by reference; ii) polymers that contain polymerized units of a vinyl phenol, an optionally substituted vinyl phenyl (e.g. styrene) that does not contain a hydroxy or carboxy ring substituent, and an alkyl acrylate such as those deblocking groups described with polymers i) above, such as polymers described in U.S. Pat. No. 6,042,997, incorporated herein by reference; iii) polymers that contain repeat units that comprise an acetal or ketal moiety that will react with photoacid, and optionally aromatic repeat units such as phenyl or phenolic groups; such polymers have been described in U.S. Pat. Nos. 5,929,176 and 6,090,526, incorporated herein by reference; (iv) polymers that comprise t-butoxycarbonyl oxy protecting (tBoc); and (v) polymer blends wherein at least one polymer of the blend comprises acid-labile groups;

2) a resin that is substantially or completely free of phenyl or other aromatic groups that can provide a chemically amplified positive resist particularly suitable for imaging at sub-200 nm wavelengths such as 193 nm. Particularly preferred resins of this class include: i) polymers that contain polymerized units of a non-aromatic cyclic olefin (endocyclic double bond) such as an optionally substituted norbornene, such as polymers described in U.S. Pat. Nos. 5,843,624, and 6,048,664, incorporated herein by reference; ii) polymers that contain alkyl acrylate units such as e.g. t-butyl acrylate, t-butyl methacrylate, methyladamantyl acrylate, methyl adamantyl methacrylate, and other non-cyclic alkyl and alicyclic acrylates; such polymers have been described in U.S. Pat. No. 6,057,083; European Published Applications EP01008913A1 and EP00930542A1; and U.S. pending patent application Ser. No. 09/143,462, all incorporated herein by reference, and iii) polymers that contain polymerized anhydride units, particularly polymerized maleic anhydride and/or itaconic anhydride units, such as disclosed in European Published Application EP01008913A1 and U.S. Pat. No. 6,048,662, both incorporated herein by reference.

3) a resin that contains repeat units that contain a hetero atom, particularly oxygen and/or sulfur (but other than an anhydride, i.e. the unit does not contain a keto ring atom), and preferable are substantially or completely free of any aromatic units. Preferably, the heteroalicyclic unit is fused to the resin backbone, and further preferred is where the resin comprises a fused carbon alicyclic unit such as provided by polymerization of a norborene group and/or an anhydride unit such as provided by polymerization of a maleic anhydride or itaconic anhydride. Such resins are disclosed in PCT/US01/14914 and U.S. Pat. No. 6,306,554.

4) a resin that contains fluorine substitution (fluoropolymer), e.g. as may be provided by polymerization of tetrafluoroethylene, a fluorinated aromatic group such as fluorostyrene compound, and the like. Examples of such resins are disclosed e.g. in PCT/US99/21912.

Suitable photoacid generators to employ in a photoresist coated over or above a coating composition of the invention include imidosulfonates such as compounds of the following formula:

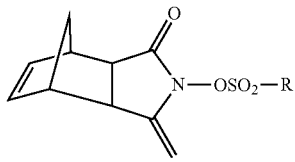

wherein R is camphor, adamantane, alkyl (e.g. CI-12 alkyl) and perfluoroalkyl such as perfluoro($C_{1-12}$alkyl), particularly perfluorooctanesulfonate, perfluorononanesulfonate and the like. A specifically preferred PAG is N-[(perfluorooctanesulfonyl)oxy]-5-norbomene-2,3-dicarboximide.

Other known PAGS also may be employed in the resists of the invention. Particularly for 193 nm imaging, generally preferred are PAGS that do not contain aromatic groups, such as the above-mentioned imidosulfonates, in order to provide enhanced transparency.

Other suitable photoacid generators for use in present photoresists include for example: onium salts, for example, triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate; nitrobenzyl derivatives, for example, 2-nitrobenzyl p-toluenesulfonate, 2,6-dinitrobenzyl p-toluenesulfonate, and 2,4-dinitrobenzyl p-toluenesulfonate; sulfonicacid esters, for example, 1,2,3-tris(methanesulfonyloxy)benzene, 1,2,3-tris(trifluoromethanesulfonyloxy)benzene, and 1,2,3-tris(p-toluenesulfonyloxy)benzene; diazomethane derivatives, for example, bis(benzenesulfonyl)diazomethane, bis(p-toluenesulfonyDdiazomethane; glyoxime derivatives, for example, bis-O-(p-toluenensulfonyl)-a-dimethylglyoxime, and bis-O-(n-butanesulfonyl)-a-dimethylglyoxime; sulfonic acid ester derivatives of an N-hydroxyimide compound, for example, N-hydroxysuccinimide methanesulfonic acid ester, N-hydroxysuccinimide trifluoromethanesulfonic acid ester; and halogen-containing triazine compounds, for example, 2-(4-methoxyphenyl)-4,6-bis(trichloromethyl)-1, 3,5-triazine, and 2-(4-methoxynaphthyl)-4,6-bis(trichloromethyl)-1,3,5-triazine. One or more of such PAGs can be used.

Photoresists for used with an underlying coating composition of the invention also may contain other materials.

A preferred optional additive of photoresists overcoated a coating composition of the invention is an added base, particularly tetrabutylammonium hydroxide (TBAH), or tetrabutylammonium lactate, which can enhance resolution of a developed resist relief image. For resists imaged at 193 nm, a preferred added base is a hindered amine such as diazabicyclo undecene or diazabicyclononene. The added base is suitably used in relatively small amounts, e.g. about 0.03 to 5 percent by weight relative to the total solids.

Other optional photoresist additives include actinic and contrast dyes, anti-striation agents, plasticizers, speed enhancers, etc. Such optional additives typically will be present in minor concentration in a photoresist composition except for fillers and dyes which may be present in relatively large concentrations such as, e.g., in amounts of from about 5 to 50 percent by weight of the total weight of a resist's dry components.

Various substituents and materials (including reaction products components and reagents to form same, resins, small molecule compounds, acid generators, etc.) as being "optionally substituted" may be suitably substituted at one or more available positions by e.g. halogen (F, Cl, Br, I); nitro; hydroxy; amino; alkyl such as $C_{1-8}$alkyl; alkenyl such as $C_{2-8}$alkenyl; alkylamino such as $C_{1-8}$ alkylamino; carbocyclic aryl such as phenyl, naphthyl, anthracenyl, etc; and the like.

Lithographic Processing

As discussed above, in use, a coating composition of the invention is applied as a coating layer to a substrate by any of a variety of methods such as spin coating. The coating composition in general is applied on a substrate with a dried layer thickness of between about 0.02 and 0.5 pm, preferably a dried layer thickness of between about 0.03 and 100 µm. The substrate is suitably any substrate used in processes involving photoresists. For example, the substrate can be silicon, silicon dioxide or aluminum-aluminum oxide microelectronic wafers. Gallium arsenide, silicon carbide, ceramic, quartz or copper substrates may also be employed. Substrates for liquid crystal display or other flat panel display applications are also suitably employed, for example glass substrates, indium tin oxide coated substrates and the like. Substrates for optical and optical-electronic devices (e.g. waveguides) also can be employed.

As discussed preferably the applied coating layer is treated (e.g. thermal treatment) to remove solvent carrier (but without significant molecular weight increases of composition component(s)) before a photoresist composition is applied over the composition layer. Thermal treatment conditions can vary with the components of the coating composition, particularly if the coating composition contains an acid or acid source such as a thermal acid generator. Suitable thermal treatment cure conditions may range from about 140° C. to 250° C. for about 0.5 to 30 minutes. Thermal conditions preferably render the coating composition coating layer substantially insoluble to solvent carrier of the overcoated photoresist composition to avoid any significant intermixing of the respective two coating layers.

After treatment of the coating composition layer, a photoresist is applied over the surface of the coating composition. As with application of the bottom coating composition, the overcoated photoresist can be applied by any standard means such as by spinning, dipping, meniscus or roller coating. Following application, the photoresist coating layer is typically dried by heating to remove solvent preferably until the resist layer is tack free.

The resist layer is then imaged with activating radiation through a mask in a conventional manner. The exposure energy is sufficient to effectively activate the photoactive component of the resist system to produce a patterned image in the resist coating layer. Typically, the exposure energy ranges from about 3 to 300 mJ/cm$^2$ and depending in part upon the exposure tool and the particular resist and resist processing that is employed. The exposed resist layer may be subjected to a post-exposure bake if desired to create or enhance solubility differences between exposed and unexposed regions of a coating layer. For example, many chemically amplified positive-acting resists require post-exposure heating to induce an acid-promoted deprotection reaction. Typically post-exposure bake conditions include temperatures of about 50° C. or greater, more specifically a temperature in the range of from about 50° C. to about 160° C.

The exposed resist coating layer is then developed, preferably with an aqueous based developer such as an alkali exemplified by tetra methylammonium hydroxide, sodium hydroxide, potassium hydroxide, sodium carbonate, sodium bicarbonate, sodium silicate, sodium metasilicate, aqueous ammonia or the like. In general, development is in accordance with art recognized procedures, except that development will also result in removal of the underlying coating composition layer in those areas underlying resist layer regions removed by the developer. Preferably, development will be terminated (e.g. by spin-drying and/or water rinse) once development of the image transferred from the resist layer is complete in the underlying coating layer to avoid excessive and undesired removal of the underlying layer, e.g. removal of the composition coating layer in areas where the resist layer is retained. Optimal development times to avoid either underdevelopment or over-development of the underlying coating composition layer can be readily determined empirically with any particular system of resist, underlying composition, developer composition and development conditions, e.g. the development can be conducted for varying times prior to termination as discussed above, and the developed images evaluated such as by scanning electron micrographs (SEMs) to determine development times or time ranges where over-development or under development does not occur.

Following development, a final bake of an acid-hardening photoresist is often employed at temperatures of from about 100° C. to about 150° C. for several minutes to further cure the developed exposed coating layer areas.

The developed substrate may then be selectively processed on those substrate areas bared of photoresist and the underlying coating composition layer, for example, chemically etching or plating substrate areas bared of photoresist in accordance with procedures well known in the art. Suitable etchants include a hydrofluoric acid etching solution and a plasma gas etch such as an oxygen plasma etch. Notably, an additional step of plasma removal of the underlying composition layer is not required where removal is accomplished in the same step as photoresist layer development, as discussed above. An implant process then can be carried out in exposed and developed areas if desired. All documents mentioned herein are incorporated herein by reference in their entirety. The following non-limiting examples are illustrative of the invention.

EXAMPLE 1

Synthesis of ANTMI Diels-Alder Cycloadduct (ANTMI) Monomer

Into a 1.0 L, 3-necked roundbottom flask, fitted with a magnetic stibar, condenser, heating mantle, and temperature controller, were added maleimide (MI, 28.7 g, 296 mmol), 9-anthracene-methyl methacrylate (ANTMA, 74.2 g, 269 mmol), hydroquinone monomethylether (MEHQ, 0.5 g, 4 mmol) and 267 g dimethylformamide. The mixture was heated to reflux at 153° C. under nitrogen gas for 12 hours.

After cooling to room temperature, the reaction mixture was diluted with 500 g of ethyl acetate. The solution was eluted through a 3-inch silica gel pad and filtered. The solution was washed with water (3×100 g) and dried over MgSO$_4$. The solvent was removed under reduced pressure at room temperature. The material was dried under vacuum for 5 hours.

72.2 g (72%) were obtained as an off-white powder. $^1$H NMR (500 MHz, dioxane-d$_8$): δ9.30 (s, 1H), 7.42-7.25 (m, 4H), 7.22-7.11 (m, 4H), 6.05 (s, 111), 5.60-5.45 (m, 3H), 4.72 (s, 1H), 3.24 (s, 2H), 1.94 (s, 3H). $^{13}$C NMR (125 MHz, dioxane-d$_8$): δ177.5, 176.9, 167.3, 143.7, 142.9, 140.4, 139.9, 137.5, 127.6, 127.2, 127.1, 126.0, 125.9, 124.7, 123.9, 67.2, 62.8, 50.1, 48.8, 46.4, 18.5.

EXAMPLES 2-3

Syntheses of ANT-MI Containing Polymers by Direct Polymerization

EXAMPLE 2

Synthesis of ANTMI Homopolymer

Into a 0.25 L, 3-necked round bottom flask, fitted with a magnetic stir bar, condenser, heating mantle, and temperature controller, were added maleimide/anthracenemethyl-methacrylate [4+2] Diels-Alder cycloadduct (ANTMI, 10.25 g, 32.7 mmol), 2,2-azobis(2,4-dimethylvaleronitrile (Vazo® 52, 0.20 g, 0.8 mmol) and 41.8 g dioxane. The reaction mixture was sparged with nitrogen gas for 15 minutes. The reaction mixture was heated to 85° C. for 12 hours.

After cooling to room temperature, the reaction mixture was diluted with 50 g dioxane and precipitated into 1.5 L of methanol. The white precipitate was isolated by vacuum filtration and dried in a vacuum oven overnight at 50° C. to give Poly(maleimide/anthracenemethylmethacrylate [4+2] Diels-Alder cycloadduct) [Poly(ANTMI)]. 7.5 g (73%) were obtained as a white powder. GPC (THF) $M_w$=26100 Da, $M_n$, =5700 Da, PDI: 4.6.

EXAMPLE 3

Synthesis of ANTMI/ANTMA 80/20 Copolymer

Into a 0.25 L, 3-necked roundbottom flask, fitted with a magnetic stirbar, condenser, heating mantle, and temperature controller, were added maleimide/anthracenemethylmethacrylate [4+2] Diels-Alder cycloadduct (ANTMI, 22.40 g, 60.0 mmol), 9-anthracene-methyl methacrylate (ANTMA, 4.11 g, 14.9 mmol), 2,2-azobis(2,4-dimethylvaleronitrile (Vazo® 52, 0.40 g, 1.6 mmol) and 54.3 g dioxane. The reaction mixture was sparged with nitrogen gas for 15 minutes. The reaction mixture was heated to 85° C. for 12 hours.

After cooling to room temperature, the reaction mixture was diluted with 60 g dioxane and precipitated into 3.0 L of methanol. The white precipitate was isolated by vacuum filtration and dried in a vacuum oven overnight at 50° C. to give Poly(maleimide/anthracenemethylmethacrylate (ANTMI)-co-9-anthracene-methyl methacrylate (ANTMA) [Poly(ANTMI)-co-(ANTMA)].

6.2 g (24%) were obtained as a white powder. GPC (THF) $M_w$=42000 Da, $M_n$, 6600 Da, PDI: 6.4.

EXAMPLES 4-6

Syntheses of ANT-MI Containing Polymer Via Polymer Modification of Pre-Polymer

EXAMPLE 4

Synthesis of ANTMA/HNMA-2/TBA 50.2/33.7/16.1 Pre-polymer

Into a 0.25 L, 3-necked round bottom flask, fitted with a magnetic stir bar, condenser, heating mantle, and temperature controller, were added 42.2 g dioxane. The solvent was sparged with nitrogen gas for 15 minutes. The solvent was heated to 85° C.

Into a 0.25 L glass bottle with stir bar were added 9-anthracene-methyl methacrylate (ANTMA, 34.67 g, 126 mmol), 2-hydroxynaphthalene-methylmethacrylate monomer (HNMA-2, 20.47 g, 84.5 mmol), t-butyl acrylate (TBA, 5.22 g, 40.7 mmol), 2,2-azobis(2,4-dimethylvaleronitrile (Vazo® 52, 1.86 g, 7.5 mmol) and dioxane (98.8 g). The mixture was allowed to stir at room temperature for 30 minutes. The solution was sparged with nitrogen gas for 15 minutes.

The monomer and initiator solution was fed to the reaction flask with a peristaltic pump over 1.2 hours at a rate of 2.1 g/min.

Upon completion of the monomer and initiator feed, a solution of 2,2-azobis(2,4-dimethylvaleronitrile (Vazo® 52, 1.24 g, 5.0 mmol) and dioxane (23.6 g) was fed to the reaction flask with a peristaltic pump over 10 minutes at a rate of 2.5 g/min.

When complete, the reaction mixture was held at 85° C. for 1.5 hours.

After cooling to room temperature, a 70 g portion of the reaction mixture was precipitated into 0.7 L of methanol. The white precipitate was isolated by vacuum filtration and dried in a vacuum oven overnight at 50° C. The remainder of the reaction mixture was utilized in the polymer modification experiments described below

EXAMPLES 5 and 6

18.2 g (92%) were obtained as a white powder. GPC (THF) $M_w$=7000 Da, $M_n$, =4200 Da, PDI: 1.6.

EXAMPLE 5

Synthesis of ANTMI/ANTMA/HNMA-2/TBA (25.1/25.1/33.7/16.1)

Modified Polymer

Into a 0.25 L, 3-necked round bottom flask, fitted with a magnetic stir bar, condenser, heating mantle, and temperature controller and containing the remaining reaction mixture from Example 4 (above) were added maleimide (MI, 4.09 g, 42.1 mmol). The reaction mixture was held at 85° C. for 6 hours.

After cooling to room temperature, a 52 g portion of the reaction mixture was diluted with 10 g dioxane and precipitated into 0.7 L of methanol. The white precipitate was isolated by vacuum filtration and dried in a vacuum oven overnight at 50° C. to give a polymer in which pendant anthracene groups are partly derivatized to ANTMI [4+2] Diels-Alder cycloadduct.

The remainder of the reaction mixture was utilized in Example 6 below. 17.2 g (100%) were obtained as a white powder. GPC (THF) $M_w$=8700 Da, $M_n$, =5000 Da, PDI: 1.7.

EXAMPLE 6

Synthesis of ANTMI/HNMA-2/TBA 50.2/33.7/16.1 Modified Polymer

Into a 0.25 L, 3-necked round bottom flask, fitted with a magnetic stir bar, condenser, heating mantle, and temperature controller and containing the remaining reaction mixture from Example 4 above, were added maleimide (MI, 2.50 g, 25.7 mmol). The reaction mixture was held at 85° C. for 6 hours.

After cooling to room temperature, the reaction mixture precipitated into 0.7 L of methanol. The white precipitate was isolated by vacuum filtration and dried in a vacuum oven overnight at 50° C. to give a polymer in which pendant anthracene groups are fully derivatized to ANTMI [4+2] Diels-Alder cycloadduct 22.7 g (74%) were obtained as a white powder. GPC (THF) $M_w$=9000 Da, $M_n$, =5100 Da, PDI: 1.8.

EXAMPLES 7-8

Syntheses of Additional ANT-MI Containing Polymers by Direct Polymerization

EXAMPLE 7

Synthesis of MI/ANTMA/HNMA-2/TBA 34.3/31.5/25.0/9.2 tetrapolymer

Into a 2.0 L, 5-necked roundbottom flask, fitted with a mechanical stirrer, condenser, heating mantle, and temperature controller, were added 215 g dioxane. The solvent was sparged with nitrogen gas for 15 minutes. The solvent was heated to 85° C.

Into a 2.0 L Erlenmeyer flask with stirbar were added maleimide (MI, 53.10 g, 547 mmol), 9-anthracene-methyl methacrylate (ANTMA, 138.7 g, 502 mmol), 2-hydroxynaphthalene-methylmethacrylate monomer (HNMA-2, 96.53 g, 398 mmol), t-butyl acrylate (TBA, 18.80 g, 147 mmol) and dioxane (423.5 g). The mixture was allowed to stir at room temperature for 30 minutes. The solution was sparged with nitrogen gas for 15 minutes.

Into a 500 mL bottle were added 2,2-azobis(2,4-dimethylvaleronitrile (Vazo® 52, 11.89 g, 48.0 mmol) and dioxane (78.0 g).

The monomer solution was fed to the reaction flask with a peristaltic pump over 1.5 hours at a rate of 8.5 g/min. The initiator solution was also fed to the reaction flask with a peristaltic pump over this period at a rate of 1.1 g/min (90 min feed).

Upon completion of the monomer and initiator feed, a solution of 2,2-azobis(2,4-dimethylvaleronitrile (Vazo® 52, 7.93 g, 32.0 mmol) and dioxane (151 g) was fed to the reaction flask with a peristaltic pump over 20 minutes at a rate of 8.2 g/min.

When complete, the reaction mixture was held at 85° C. for 1.5 hours.

After cooling to room temperature, the reaction mixture was precipitated into 15.0 L of methanol. The white precipitate was isolated by vacuum filtration, washed with 3.0 L of methanol and dried in a vacuum oven overnight at 50° C.

195.1 g (64%) of the title polymer was obtained as a white powder. GPC (THF) $M_w$=9300 Da, $M_n$=6500 Da, PDI: 1.5.

EXAMPLE 8

Synthesis of MI/ANTMA/HNMA-2/TBA 33.2/31.3/26.8/8.7 tetrapolymer

Into a 2.0 L, 5-necked roundbottom flask, fitted with a mechanical stirrer, condenser, heating mantle, and temperature controller, were added 218 g dioxane. The solvent was sparged with nitrogen gas for 15 minutes. The solvent was heated to 85° C.

Into a 2.0 L Erlenmeyer flask with stirbar were added maleimide (MI, 51.39 g, 529 mmol), 9-anthracene-methyl methacrylate (ANTMA, 137.9 g, 499 mmol), 2-hydroxynaphthalene-methylmethacrylate monomer (HNMA-2, 103.4 g, 427 mmol), t-butyl acrylate (TBA, 17.82 g, 139 mmol) and dioxane (430 g). The mixture was allowed to stir at room temperature for 30 minutes. The solution was sparged with nitrogen gas for 15 minutes.

Into a 500 mL bottle were added 2,2-azobis(2,4-dimethylvaleronitrile (Vazo® 52, 11.89 g, 48.0 mmol) and dioxane (78.0 g).

The monomer solution was fed to the reaction flask with a peristaltic pump over 1.5 hours at a rate of 7.5 g/min. The initiator solution was also fed to the reaction flask with a peristaltic pump over this period at a rate of 0.9 g/min (90 min feed).

Upon completion of the monomer and initiator feed, a solution of 2,2-azobis(2,4-dimethylvaleronitrile (Vazo® 52, 7.93 g, 32.0 mmol) and dioxane (151 g) was fed to the reaction flask with a peristaltic pump over 20 minutes at a rate of 8.2 g/min.

When complete, the reaction mixture was held at 85° C. for 1.5 hours.

After cooling to room temperature, the reaction mixture was precipitated into 15.0 L of methanol. The white precipitate was isolated by vacuum filtration, washed with 3.0 L of methanol and dried in a vacuum oven overnight at 50° C.

186.6 g (60%) of the title polymer was obtained as a white powder. GPC (THF) $M_w$=9200 Da, $M_n$=6350 Da, PDI: 1.5.

EXAMPLE 9

Coating Composition Preparation and Lithographic Processing

An underlying coating composition is prepared by admixing the following materials:
Resin
Polymer of Example 5 above
Photoacid generator
triphenyl sulfonium salt
Solvent
ethyl lactate The resin is present in an amount of 5 grams. The photoacid generator compound is present in an amount of about 0.5 weight percent of total solids (all components expect solvent).

This formulated coating composition is spin coated onto a silicon microchip wafer and is cured at 210° C. for 60 seconds on a vacuum hotplate to provide a dried (but not cross-linked) coating layer.

A commercially available 193 nm positive-acting photoresist is then spin-coated over the cured coating composition layer. The applied resist layer is soft-baked at 100° C. for 60 seconds on a vacuum hotplate, exposed to patterned 193 nm radiation through a photomask, post-exposure baked at 110° C. for 60 seconds and then developed with 0.26 N aqueous alkaline developer where both the photoresist later and underlying coating composition are removed in areas defined by the photomask.

EXAMPLE 10

Coating Composition Preparation and Lithographic Processing

An underlying coating composition is prepared by admixing the following materials:
Resin
Polymer of Example 6 above
Photoacid generator
triphenyl sulfonium salt
Solvent
ethyl lactate The resin is present in an amount of 5 grams. The photoacid generator compound is present in an amount of about 0.5 weight percent of total solids (all components expect solvent).

This formulated coating composition is spin coated onto a silicon microchip wafer and is cured at 210° C. for 60 seconds on a vacuum hotplate to provide a dried (but not cross-linked) coating layer.

A commercially available 193 nm positive-acting photoresist is then spin-coated over the cured coating composition layer. The applied resist layer is soft-baked at 100° C. for 60 seconds on a vacuum hotplate, exposed to patterned 193 nm radiation through a photomask, post-exposure baked at 110° C. for 60 seconds and then developed with 0.26 N aqueous alkaline developer where both the photoresist later and underlying coating composition are removed in areas defined by the photomask.

EXAMPLE 11

Coating Composition Preparation and Lithographic Processing

An underlying coating composition is prepared by admixing the following materials:
Resin
Polymer of Example 7 above
Photoacid generator
triphenyl sulfonium salt
Solvent
ethyl lactate The resin is present in an amount of 5 grams. The photoacid generator compound is present in an amount of about 0.5 weight percent of total solids (all components expect solvent).

This formulated coating composition is spin coated onto a silicon microchip wafer and is cured at 210° C. for 60 seconds on a vacuum hotplate to provide a dried (but not cross-linked) coating layer.

A commercially available 193 nm positive-acting photoresist is then spin-coated over the cured coating composition layer. The applied resist layer is soft-baked at 100° C. for 60 seconds on a vacuum hotplate, exposed to patterned 193 nm radiation through a photomask, post-exposure baked at 110° C. for 60 seconds and then developed with 0.26 N aqueous alkaline developer where both the photoresist later and underlying coating composition are removed in areas defined by the photomask.

EXAMPLE 12

Coating Composition Preparation and Lithographic Processing

An underlying coating composition is prepared by admixing the following materials:
Resin
Polymer of Example 8 above
Photoacid generator
triphenyl sulfonium salt
Solvent
ethyl lactate The resin is present in an amount of 5 grams. The photoacid generator compound is present in an amount of about 0.5 weight percent of total solids (all components expect solvent).

This formulated coating composition is spin coated onto a silicon microchip wafer and is cured at 210° C. for 60 seconds on a vacuum hotplate to provide a dried (but not cross-linked) coating layer.

A commercially available 193 nm positive-acting photoresist is then spin-coated over the cured coating composition layer. The applied resist layer is soft-baked at 100° C. for 60 seconds on a vacuum hotplate, exposed to patterned 193 nm radiation through a photomask, post-exposure baked at 110° C. for 60 seconds and then developed with 0.26 N aqueous alkaline developer where both the photoresist later and underlying coating composition are removed in areas defined by the photomask.

EXAMPLE 13

Coating Composition Preparation and Lithographic Processing

An underlying coating composition is prepared by admixing the following materials:
Resin
Polymer Blend from Examples 7 and 8 above
Photoacid generator
triphenyl sulfonium salt
Solvent
ethyl lactate The resins are present in equal weight amounts for a combined weight of 5 grams. The photoacid generator compound is present in an amount of about 0.5 weight percent of total solids (all components expect solvent).

This formulated coating composition is spin coated onto a silicon microchip wafer and is cured at 210° C. for 60 seconds on a vacuum hotplate to provide a dried (but not cross-linked) coating layer.

A commercially available 193 nm positive-acting photoresist is then spin-coated over the cured coating composition layer. The applied resist layer is soft-baked at 100° C. for 60 seconds on a vacuum hotplate, exposed to patterned 193 nm radiation through a photomask, post-exposure baked at 110° C. for 60 seconds and then developed with 0.26 N aqueous alkaline developer where both the photoresist later and underlying coating composition are removed in areas defined by the photomask.

EXAMPLE 14

Additional Coating Composition and Lithographic Processing

A coating composition is prepared by admixing the following components: materials:
Resins
Polymer Blend from Examples 7 and 8 above
Photoacid generator
triphenyl sulfonium salt
Solvent
methyl 2-hydroxyisobutyrate In this coating composition, the resins are present in equal weight amounts for a combined weight of 3.2 grams and the photoacid generator is present at about 2% weight percent of total solids (all materials except solvent). The solvent is present in an amount of about 96 weight percent of the total coating composition weight.

This coating composition is spin coated onto a silicon wafer substrate and baked at 215° C. to remove solvent, but does not result in crosslinking of the coating composition layer.

EXAMPLE 15

Test to Confirm That Thermal Treatment of an Underlying Coating Composition Does Not Result In Crosslinking (Molecular Weight Increase of Composition Components)

A solution of a polymer containing polymerized units of maleimide, polyhydroxystyrene and 9-anthracene-methyl methacrylate were spin cast onto 8" silicon wafers and baked at 180° C. and 240° C. An unbaked coating of each material was also prepared. Formulations containing the same polymer but also a photoacid generator compound were also prepared and coatings were made on 8" silicon wafers at the same bake temperatures (room temperature, 180° C. and 240° C.). After processing as described above, all of the coated films were scraped, readily dissolved in THF and molecular weight measured by GPC.

The weight-average molecular weight data for the polymer films with and without PAG showed minimal change after thermal processing thus indicating that crosslinking did not take place upon the thermal treatments.

EXAMPLE 16

Monomer Synthesis

Scheme 3 below in this Example illustrates he synthesis of a polymerizable methacrylate monomer with a pendant 6-HNA chromophore. This monomer can be prepared in two steps from 6-hydroxy-2-naphthanoic acid.

Scheme 3. Synthesis of 6-HNA containing monomer 1. (a) thionyl chloride, THF, RT, 1 hr. (b) 2-hydroxyethylmethacrylate, triethylamine, THF, 0° C. to RT, 18 hrs.

EXAMPLE 17

Sequential Post-Polymerization Modification of a Multi-Functional Poly(Acrylate) to Introduce a Pendant 6-HNA Chromophore and the Desired DBARC Performance Characteristics In Scheme 4 immediately below, the sequential modification of a multi-functional poly(acrylate) pre-polymer, polymer 7 is illustrated.

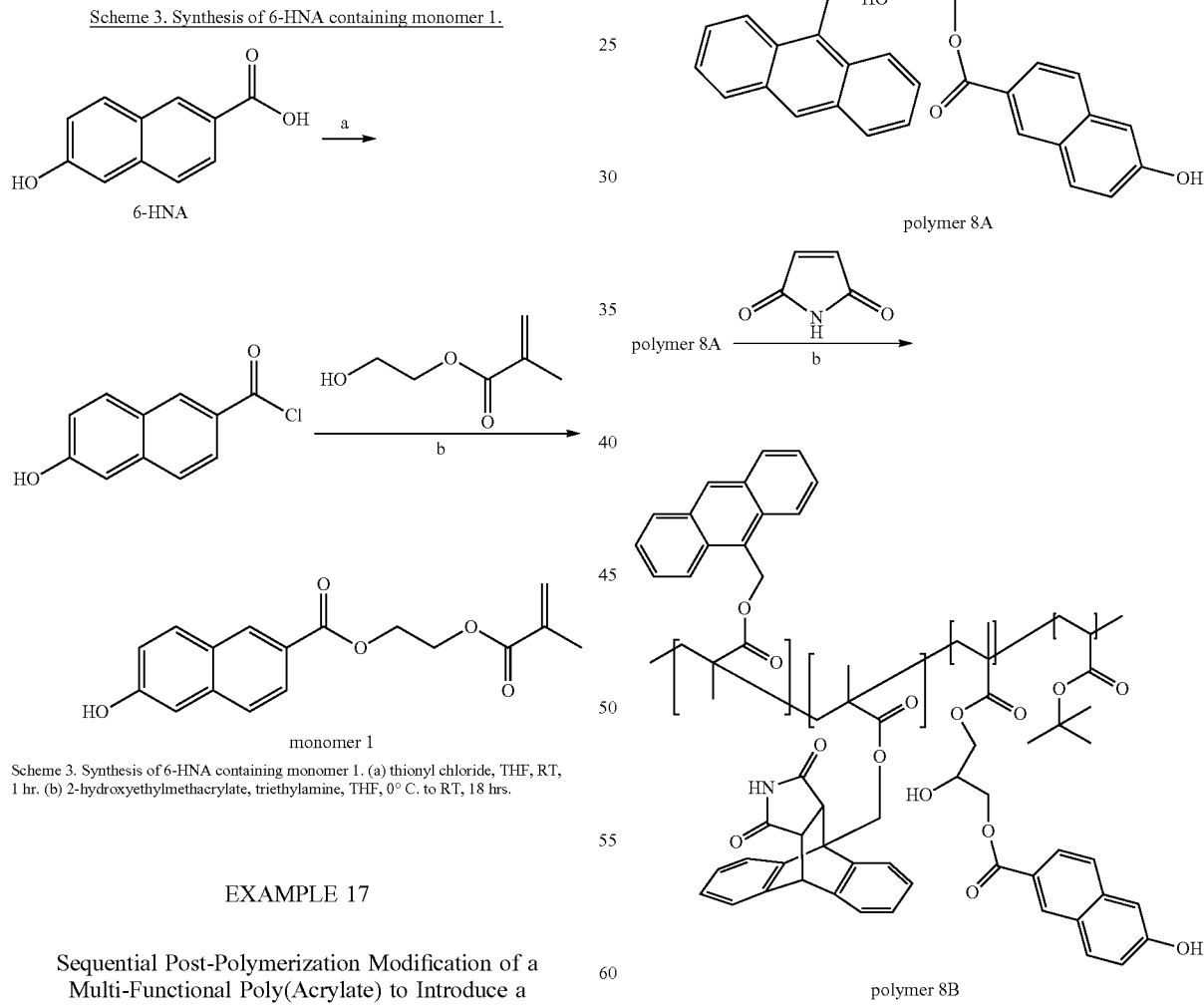

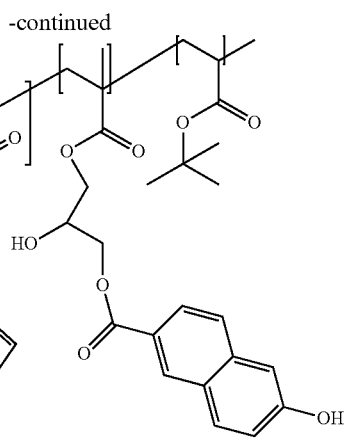

polymer 8C

Sequential polymer modification of poly(acrylate), 7, with 6-hydroxy-2-naphthoic acid to afford a chromophore modified polymer 8A. Subsequent Diels-Alder modification of polymer 8A with 0.55 equiv. maleimide (based on anthracene content) to afford a functional DBARC poly(acrylate), 8B. Subsequent Diels-Alder modification of polymer 8B with 1 equiv. maleimide (based on anthracene content) to afford a functional DBARC poly(acrylate), 8C. (a) 6-hydroxy-2-naphthoic acid, benzyltriethylaramonium chloride, dioxane, DMF, 85° C., 12 hrs; (b) maleimide, 85° C., 6 hrs (same reactor); (c) maleimide, 85° C., 6 hrs (same reactor).

In the following discussion, reference numerals indicate those materials of the same number as set forth in Scheme 4 above. Upon treatment of the epoxy-function polymer 7 with 6-hydroxy-2-naphthoic acid (6-HNA), in the presence of a catalyst (benzyl triethyl ammonium chloride), the carboxylic acid undergoes an epoxy ring opening reaction with the pendant glycidyl groups in polymer 7 to afford the modified polymer 8A. The ratio of 6-HNA, polymer 7, the catalyst, and the temperature may be varied to control the degree of 6-HNA attachment in the polymer. The optical properties of the resulting modified polymer, 8A, are modified by the attachment of the pendant 6-HNA groups to afford the desired absorption (k value) at 248 nm.

Both pre-polymer 7 and 6-HNA modified-polymer 8A present a diene functionality, the pendant anthracene group. This anthracene group does not react under the conditions presented for the 6-HNA attachment reaction. In addition, the reagents present in the reaction mixture will not interfere with any subsequent Diels-Alder reaction between the anthracene group and maleimide. As a result, we regard polymer 7 as a multifunctional material with two pendant and selective functional groups (the epoxy and the anthracene). We note that no isolation of intermediate polymers is necessary, and the entire process can be done in a single reactor.

Upon treatment of polymer 8A with 0.55 equivalents of maleimide (MI, based on anthracene content in pre-polymer 8A) and heating, a Diels-Alder reaction occurs between the pendant anthracene groups and the maleimide to afford a modified polymer, 8B. The ratio of maleimide to the pendant anthracene groups in polymer 8A, and the reaction temperature may be varied to control the degree of formation of pendant maleimide/anthracene cyclo-adducts in the polymer.

Polymer 8B was further reacted with 1.0 equivalents of maleimide (MI, based on anthracene content in pre-polymer 8B) and upon heating, a Diels-Alder reaction occurs between the pendant anthracene groups and the maleimide to afford a modified polymer, 8C.

An initial evaluation of the optical and physical properties of polymers 7, 8A, 8B, and 8C is underway. The results of an initial evaluation of these materials is provided in Table 1. From the VASE data, we find that k value at 248 nm is decreased as the level of maleimide attachment in the polymer is increased (0.64 for 8A to 0.20 for 8C). From the solvent strip test data, we find that all polymers demonstrate acceptable solvent strip resistance. For the 8C sample, we find that the dissolution rate in aqueous developer is higher than that of polymers 8B and 8A. Further investigation is warranted and necessary to afford the desired optical properties and performance characteristics for advanced photolithographic applications.

TABLE 1

Polymer optical properties and solvent/developer strip test data.

| Sample | Solvent | Solvent strip data (Å loss) | CD-26 strip data 30 seconds (Å loss) | n/k data |
|---|---|---|---|---|
| 8A | Ethyl lactate | 0 | 0 | 193 nm 1.61/0.195 248 nm 1.522/0.637 |
| 8B | PGMEA | −1@ 210 C. | 0 | 193 nm 1.68/0.38 248 nm 1.70/0.253 |
| 8C | PGMEA | −2@ 210 C. | −15 | 193 nm 1.68/0.410 248 nm 1.74/0.199 |

EXAMPLE 18

In Scheme 5 immediately below the synthesis of a polymerizable methacrylast monomer, 2, with a pendant 6-HNA chromophore is illustrated. This monomer can be prepared in three steps from 6-hydroxy-2-naphthanoic acid. UV is absorption data is illustrated in Scheme 5.

Scheme 5. Synthesis of 6-HNA containing monomer 2.

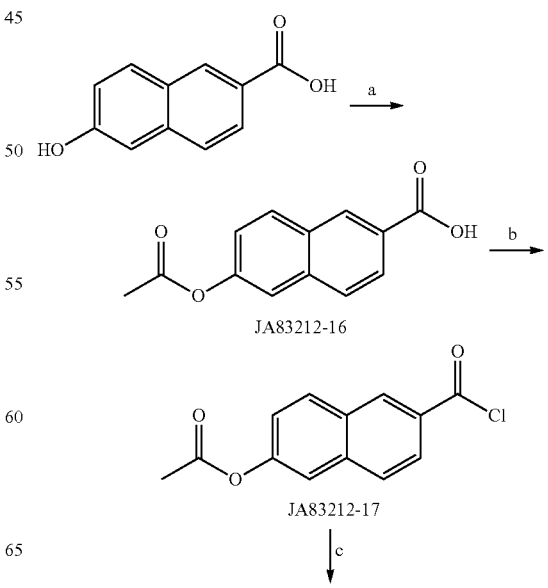

JA83212-16

JA83212-17

-continued

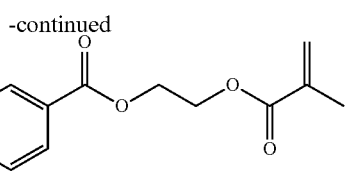

JA83212-20

(a) acetic anhydride, pyridine, 0° C. to RT, 12 hrs, 92% (b) thionyl chloride, DMF (cat.), reflux, 1 hr, 95% (c) 2-hydroxyethylmethacrylate, thiethylamine, THF, 0° C. to RT, 12 hrs, 81%.

EXAMPLE 19

Synthesis of 6-Acetoxy-2-Naphthoic Acid

Into a 0.25 L, 3-necked roundbottom flask, fitted with a magnetic stirbar and addition funnel were added 6-hydroxy-2-naphthoic acid (20.0 g, 106 mmol) and pyridine (100 mL, 1.24 mol). The reaction mixture was cooled to 0° C. in an ice water bath. Acetic anhydride (10.9 g, 106 mmol) was added dropwise over 15 minutes. The reaction mixture was allowed to warm to room temperature and stirred for 18 hours.

The reaction mixture was poured into 1.1 L of a 10:1 mixture of water and concentrated hydrochloric acid. The white precipitate was isolated by vacuum filtration and washed with an additional 1 L of water. The white solid was allowed to air dry over 48 hours.

22.5 g (92%) were obtained as a white powder.

$^1$H NMR (500 MHz, DMSO-$d_6$): δ13.10 (s, br, 1H), 8.65 (s, 1H), 8.17 (d, 1H, J=10), 8.05 (dd, 2H, J=10, 20), 7.75 (s, 1H), 7.40 (m, 1H), 2.38 (s, 311). $^{13}$C NMR (125 MHz, DMSO-$d_6$): δ169.5, 167.5, 150.0, 135.5, 131.0, 130.5, 130.2, 127.9, 127.8, 126.0, 122.6, 118.6, 21.0.

EXAMPLE 20

Synthesis of 6-Acetoxy-2-Naphthoic Acid Chloride

Into a 0.25 L, 3-necked roundbottom flask, fitted with a magnetic stirbar, addition funnel, and reflux condenser were added 6-acetoxy-2-naphthoic acid (30.0 g, 130 mmol), THF (135 mL) and dimethylformamide (approx. 20 drops). Thionyl chloride (18.6 g, 156 mmol) was added slowly dropwise to the reaction mixture over 15 minutes. The reaction mixture was heated to reflux for 2.5 hours under nitrogen and allowed to cool to room temperature overnight.

The reaction mixture was evaporated to dryness under reduced pressure at room temperature. Toluene (50 g) was added and the reaction mixture was again evaporated to dryness under reduced pressure at room temperature. Another 50 g portion of toluene was added and the reaction mixture was again evaporated to dryness under reduced pressure at room temperature. The off-white solid was triturated with hexanes. The off-white powder was isolated by vacuum filtration.

31.3 g (96%) were obtained as an off-white powder.

$^1$1-lNMR (500 MHz, CDCl$_3$): δ8.63 (s, 1H), 7.95 (m, 2H), 7.77 (m, 1H), 7.58 (s, 1H), 7.32 (m, 1H), 2.40 (s, 3H). $^{13}$C NMR (125 MHz, CDCl$_3$): δ169.2, 168.2, 151.5, 137.0, 134.5, 131.6, 130.2, 130.1, 128.5, 126.0, 123.0, 118.8, 21.8.

EXAMPLE 21

Synthesis of 6-Acetoxy-Naphthalene-2-Carboxylic Acid 2-(2-Methyl-Aciyloyloxy)-Ethyl Ester (ANNA-3)

Into an oven-dried 0.25 L, 3-necked roundbottom flask, fitted with a magnetic stirbar and addition funnel under nitrogen were added a solution of hydroxyethylmethacrylate (3.90 g, 30 mmol) and triethylamine (3.40 g, 34 mmol) in THF (40 mL). The reaction mixture was cooled to 0° C. in an ice water bath. A solution of 6-acetoxy-2-naphthoic acid chloride (7.0 g, 28 mmol) in THF (80 mL) was added slowly dropwise to the reaction mixture over 1.5 hours. The reaction mixture was allowed to warm to room temperature and stirred for 18 hours.

The reaction mixture was poured into water (300 mL) and extracted with ethyl acetate (100 mL). The organic extract was washed with water (100 mL), 1% sodium bicarbonate solution (2×100 mL) and dried over magnesium sulfate. The organic extract was evaporated to dryness under reduced pressure at 30° C. An amber oil was obtained that solidified upon standing. The material is 95% pure by HPLC-MS. The crude material was used without additional purification.

7.8 g (81%) were obtained as a waxy solid.

$^1$H NMR (500 MHz, CDCl$_3$): δ8.62 (s, 1H), 8.04 (m, 2H), 7.89 (m, 1H), 7.64 (s, 1H), 7.33 (m, 1H), 6.10 (s, 1H), 5.58 (s, 1H), 4.60 (m, 214), 4.49 (m, 211), 2.30 (s, 3H), 1.90 (s, 314). $^{13}$C NMR (125 MHz, CDCl$_3$): δ169.4, 167.3, 166.5, 151.3, 137.3, 136.9, 131.5,131.4, 131.3, 128.6, 128.1, 126.6, 125.8, 123.0, 119.2, 63.6, 63.4, 21.0, 18.4.

EXAMPLE 22

Synthesis of MI/ANTMA/HNMA-3/7'BA 30.7/29.0/31.8/8.5 Tetrapolymer

Into a 0.25 L, 3-necked roundbottom flask, fitted with a magnetic stirbar, condenser, heating mantle, and temperature controller, were added 20 g propylene glycol monomethyl ether (PGME). The solvent was sparged with nitrogen gas for 15 minutes. The solvent was heated to 85° C.

Into a 0.5 L Erlenmeyer flask with stirbar were added maleimide (MI, 3.73 g, 38 mmol), 9-anthracene-methyl methacrylate (ANTMA, 10.00 g, 36 mmol), 6-Acetoxy-naphthalene-2-carboxylic acid 2-(2-methyl-acryloyloxy)-ethyl ester (ANMA-3, 13.61 g, 40 mmol), t-butyl acrylate (TBA, 1.36 g, 11 mmol) and PGME (30 g). The mixture was allowed to stir at room temperature for 30 minutes. The solution was sparged with nitrogen gas for 15 minutes. Into a 100 mL bottle were added 2,2-azobis(2,4-dimethylvaleronitrile (Vazo® 52, 0.93 g, 4 mmol) and PGME (16 g).

The monomer solution was fed to the reaction flask with a peristaltic pump over 1.5 hours at a rate of 0.6 g/min. The initiator solution was also fed to the reaction flask with a peristaltic pump over this period at a rate of 0.2 g/min (90 min feed).

Upon completion of the monomer and initiator feed, a solution of 2,2-azobis(2,4-dimethylvaleronitrile (Vazo® 52, 0.62 g, 2 mmol) and PGME (12 g) was fed to the reaction flask with a peristaltic pump over 20 minutes at a rate of 0.7 g/min.

When complete, the reaction mixture was held at 85° C. for 1.5 hours.

Acetoxy-de-protection: A solution of ammonium acetate (6.20 g, 80 mmol) and water (3.60 mL, 200 mmol) was added to the reaction mixture. The reaction was heated at 85° C. for 12 hours.

After cooling to room temperature, the reaction mixture was precipitated into 1.0 L of methanol. The white precipitate was isolated by vacuum filtration, washed with 1.0 L of methanol and dried in a vacuum oven overnight at 50° C.

20.7 g (77%) were obtained as a white powder.

EXAMPLE 23

Coating Composition Preparation and Lithographic Processing

An underlying coating composition is prepared by admixing the following materials:

Resin

Polymer 8B depicted in Scheme 4 above

Photoacid generator triphenyl sulfonium salt

Solvent ethyl lactate

The resin is present in an amount of 5 grams. The photoacid generator compound is present in an amount of about 0.5 weight percent of total solids (all components expect solvent).

This formulated coating composition is spin coated onto a silicon microchip wafer and is cured at 210° C. for 60 seconds on a vacuum hotplate to provide a dried (but not cross-linked) coating layer.

A commercially available 193 nm positive-acting photoresist is then spin-coated over the cured coating composition layer. The applied resist layer is soft-baked at 100° C. for 60 seconds on a vacuum hotplate, exposed to patterned 193 tun radiation through a photomask, post-exposure baked at 110° C. for 60 seconds and then developed with 0.26 N aqueous alkaline developer where both the photoresist later and underlying coating composition are removed in areas defined by the photomask.

The foregoing description of this invention is merely illustrative thereof, and it is understood that variations and modifications can be made without departing from the spirit or scope of the invention as set forth in the following claims.

What is claimed is:

1. An antireflective composition for use with an overcoated photoresist, the antireflective composition comprising:
    a resin comprising a Diets Alder reaction product; and
    a component comprising a hydroxyl-naphthoic group.

2. The composition of claim 1 wherein the antireflective composition resin comprises a reaction product of an imide-containing dienophile and a polycyclic aromatic group.

3. The composition of claim 1 wherein the antireflective composition resin comprises a reaction product of (1) an imide-containing dienophile and (2) an anthraecene or pentacene group.

4. The composition of claim 1 which comprises a compound that comprises one or more repeat units that comprise one or more groups of the following formulae:

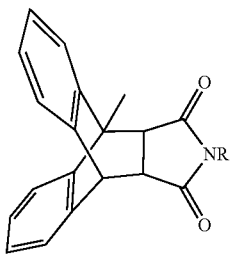

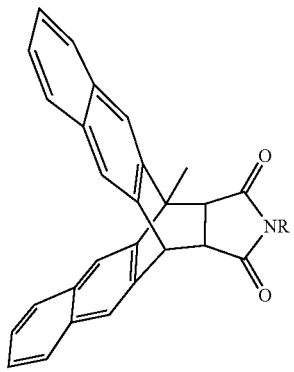

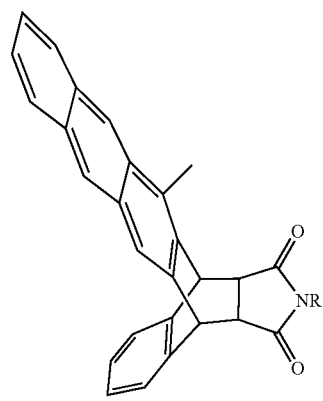

wherein in the above formulae each R is independently hydrogen or a non-hydrogen substitutent.

5. The composition of claim 1 wherein the composition comprises a resin that comprises one or more repeat units that comprise one or more groups of the following formulae:

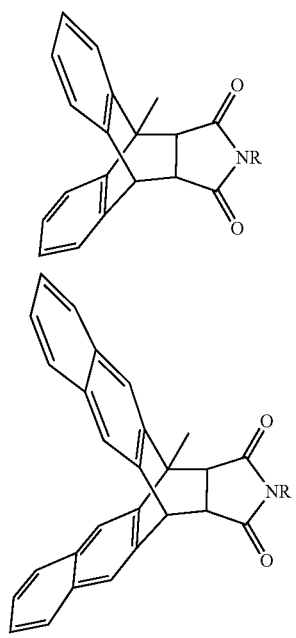

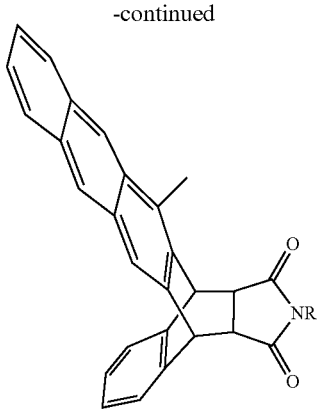

wherein in the above formulae each R is independently hydrogen or a non-hydrogen substitutent.

6. The composition of claim 1 wherein the coating composition comprises a resin comprising a 6-hydroxy-2-naphthoic group.

7. The composition of claim 1 wherein the composition comprises a resin that comprises moieties that comprises (i) a reaction product of a diene and a dienophile and (ii) a hydroxyl-naphthoic group.

* * * * *